(12) United States Patent
Gowda et al.

(10) Patent No.: US 7,412,141 B2
(45) Date of Patent: Aug. 12, 2008

(54) LIGHT DIFFUSING TIP

(75) Inventors: Ashok Gowda, Houston, TX (US); Roger J. McNichols, Pearland, TX (US); Marc Gelnett, Houston, TX (US); Matthew Fox, Bellaire, TX (US)

(73) Assignee: Biotex, Inc., Houston, TX (US)

( * ) Notice: Subject to any disclaimer, the term of this patent is extended or adjusted under 35 U.S.C. 154(b) by 0 days.

(21) Appl. No.: 11/777,856

(22) Filed: Jul. 13, 2007

(65) Prior Publication Data

US 2008/0015560 A1 Jan. 17, 2008

Related U.S. Application Data

(62) Division of application No. 10/989,894, filed on Nov. 16, 2004, now Pat. No. 7,274,847.

(51) Int. Cl.
G02B 6/06 (2006.01)
A61B 18/18 (2006.01)

(52) U.S. Cl. .................. 385/117; 385/139; 606/15; 606/16

(58) Field of Classification Search ............... 385/117
See application file for complete search history.

(56) References Cited

U.S. PATENT DOCUMENTS

| | | | |
|---|---|---|---|
| 4,140,130 A | 2/1979 | Storm, III | |
| 4,466,697 A | 8/1984 | Daniel | |
| 4,585,298 A | 4/1986 | Mori | |
| 4,660,952 A | 4/1987 | Toyoda et al. | |
| 4,669,467 A | 6/1987 | Willett et al. | |
| 4,693,556 A | 9/1987 | McCaughan | |
| 4,785,815 A | 11/1988 | Cohen | |
| 4,832,024 A | 5/1989 | Boussignac et al. | |
| 4,852,567 A | 8/1989 | Sinofsky | |
| 4,862,887 A | 9/1989 | Weber et al. | |
| 4,959,063 A | 9/1990 | Kojima | |

(Continued)

FOREIGN PATENT DOCUMENTS

DE 4137983 11/1991

OTHER PUBLICATIONS

Weber et al., "Laser versus Radiofrequency Catheter Ablation of Ventricular Myocardium in Dogs: A COmparative Test," Cardiology, vol. 88, 1997, pp. 346-352.

(Continued)

Primary Examiner—Frank G Font
Assistant Examiner—Mary A El Shammaa

(57) ABSTRACT

A light diffusing tip is provided. The light diffusing tip comprises a housing and a monolithic light scattering medium disposed within the housing. The monolithic light scattering medium comprises a first scattering region at a first position, the scattering region having a first scattering property and a second scattering region at a second position, the second scattering region having a second scattering property different from the first scattering property, wherein the first scattering region and the second scattering region are coextensive along a substantial portion of a length of the housing. A light diffusing applicator also is provided. The light diffusing applicator comprises at least one optical waveguide, a first termination coupled to a first end of the at least one optical waveguide, the first termination to couple to a light source and a light diffusing tip coupled to a second end of the at least one optical waveguide.

22 Claims, 7 Drawing Sheets

U.S. PATENT DOCUMENTS

| | | | |
|---|---|---|---|
| 4,986,628 A | 1/1991 | Lozhenko et al. | |
| 5,042,980 A | 8/1991 | Baker et al. | |
| 5,061,265 A | 10/1991 | Abela et al. | |
| 5,074,632 A | 12/1991 | Potter | |
| 5,151,096 A | 9/1992 | Khoury | |
| 5,169,396 A | 12/1992 | Dowlatshahi et al. | |
| 5,196,005 A | 3/1993 | Doiron et al. | |
| 5,207,669 A | 5/1993 | Baker et al. | |
| 5,219,346 A | 6/1993 | Wagnieres et al. | |
| 5,246,436 A | 9/1993 | Rowe | |
| 5,269,777 A * | 12/1993 | Doiron et al. | 606/7 |
| 5,292,320 A | 3/1994 | Brown et al. | |
| 5,303,324 A | 4/1994 | Lundahl | |
| 5,312,392 A | 5/1994 | Hofstetter et al. | |
| 5,330,465 A * | 7/1994 | Doiron et al. | 606/7 |
| 5,337,381 A | 8/1994 | Biswas et al. | |
| 5,348,552 A | 9/1994 | Nakajima et al. | |
| 5,363,458 A | 11/1994 | Pan et al. | |
| 5,373,571 A | 12/1994 | Reid et al. | |
| 5,429,635 A | 7/1995 | Purcell, Jr. et al. | |
| 5,431,647 A | 7/1995 | Purcell, Jr. et al. | |
| 5,441,497 A * | 8/1995 | Narciso, Jr. | 606/15 |
| 5,454,807 A | 10/1995 | Lennox et al. | |
| 5,496,308 A | 3/1996 | Brown et al. | |
| 5,520,681 A | 5/1996 | Fuller et al. | |
| 5,530,780 A | 6/1996 | Ohsawa | |
| 5,536,265 A | 7/1996 | van den Bergh et al. | |
| 5,545,161 A | 8/1996 | Imran | |
| 5,607,421 A | 3/1997 | Jeevanandam et al. | |
| 5,688,263 A | 11/1997 | Hauptmann et al. | |
| 5,754,717 A | 5/1998 | Esch | |
| 5,792,100 A | 8/1998 | Shantha | |
| 5,807,390 A | 9/1998 | Fuller et al. | |
| 5,824,005 A | 10/1998 | Motamedi et al. | |
| 5,830,196 A | 11/1998 | Hicks | |
| 5,871,521 A | 2/1999 | Kaneda et al. | |
| 5,906,606 A | 5/1999 | Chee et al. | |
| 5,908,415 A | 6/1999 | Sinofsky | |
| 5,946,441 A | 8/1999 | Esch | |
| 5,947,959 A | 9/1999 | Sinofsky | |
| 5,978,541 A * | 11/1999 | Doiron et al. | 385/139 |
| 5,997,571 A | 12/1999 | Farr et al. | |
| 6,004,315 A | 12/1999 | Dumont | |
| 6,071,302 A * | 6/2000 | Sinofsky et al. | 607/88 |
| 6,102,905 A | 8/2000 | Baxter et al. | |
| 6,106,514 A | 8/2000 | O'Donnell, Jr. | |
| 6,212,426 B1 | 4/2001 | Swanson | |
| 6,270,492 B1 * | 8/2001 | Sinofsky | 606/15 |
| 6,283,958 B1 | 9/2001 | Vogl et al. | |
| 6,343,174 B1 | 1/2002 | Neuberger | |
| 6,361,530 B1 | 3/2002 | Mersch | |
| 6,383,179 B1 | 5/2002 | Neuberger | |
| 6,418,252 B1 | 7/2002 | Maitland | |
| 6,503,246 B1 | 1/2003 | Har-Shai et al. | |
| 6,554,824 B2 | 4/2003 | Davenport et al. | |
| 6,576,163 B2 | 6/2003 | Mersch | |
| 7,270,656 B2 | 9/2007 | Gowda et al. | |

OTHER PUBLICATIONS

Welch et al., "Evaluation of Cooling Techniques for the Protection of the Epidermis During Nd: YAG Laser Irradiation of the Skin," in Neodymium-YAG Laser in Medicine and Surgery, S.N. Joffe, Ed. New York: Elsevier, 1983, pp. 196-204.

U.S. Appl. No. 10/208,222, filed Jul. 30, 2002, entitled "Cooled Tip Laser Catheter for Sensing and Ablation of Cardiac Arrhythmias".

* cited by examiner

A

B

C

LIGHT DIFFUSING TIP

CROSS-REFERENCE TO RELATED APPLICATION(S)

The present application is a divisional application of and claims priority from U.S. patent application Ser. No. 10/989,894, filed Nov. 16, 2004, entitled "LIGHT DIFFUSING TIP," naming inventors Ashok Gowda, Roger McNichols, Marc Gelnett, and Mathew Fox, which application is incorporated by reference herein in its entirety.

FIELD OF THE DISCLOSURE

The present disclosure relates generally to fiber optic light applicators and more particularly to light diffusion devices.

BACKGROUND

Light diff-using tip applicators find application in a number of clinical settings. Prevalent uses include the treatment of cancerous tumors using either photodynamic therapy (PDT) or laser interstitial thermal therapy (LITT). In PDT, light diff-using fiber optics are used to uniformly irradiate an organ or tissue that has been previously treated with a photo-sensitive light-activated compound which has been allowed to accumulate in the tumor. In LITT, laser energy is applied to tissues for treating solid malignant tumors in various organs such as the liver, brain, ear nose or throat (ENT), or abdominal tissues, as well as for treating benign alterations such as prostate adenomas, Volumetric heating within target tissues during LITT results in thermal tissue necrosis and tumor death.

Light diffusing tip applicators used to carry light from a source into a target tissue during such therapies can vary significantly in terms of their size and shape, as well as the way that they distribute light. A conventional bare fiber optic that terminates in a cleaved or polished face perpendicular to the optic axis is limited in most PDT and LITT procedures. To illustrate, for, LITT procedures the power density and resulting heat generation using a bare fiber often exceed the thermal diffusion into the tissue, and areas close to the applicator therefore char or vaporize. These tissue phenomena are problematic for creating controlled photothermal lesions For example, charring limits heat deposition within deeper tissue volumes due to increased absorption of light energy by the charred region. As charred tissue continues to absorb incident light, its temperature continues to rise leading to more carbonization around the applicator, and temperature rise in deeper layers is strictly dependent on heat conduction away from this carbonized volume. While it is possible to create large thermal lesions in this manner, the morphology of the resulting lesion is highly undesirable. Furthermore, the high temperatures associated with the carbonized tissue often result in burning and failure at the tip of the optical fiber with significant attendant risk for patients and equipment. Therefore, many LITT procedures employ an applicator with a light diffuser (or diffusing tip) at the delivery end of the optical fiber. In such applications, the scattering of light over a larger surface area provided by the diffusing tip reduces the power density on the adjacent tissue and creates a larger coagulation volume while minimizing char formation, Several techniques have been developed to obtain scattering of light from an optical fiber. One conventional technique includes selecting the ratio of the index of refraction between the core of the optical fiber and the transparent cladding such that total internal reflection is prevented, thereby allowing light to escape and radiate outside of the fiber. It is difficult, however, to achieve uniform output intensity using this method, and its use therefore is not widespread. Other conventional techniques include etching the outer surface of the core or clad using chemical or mechanical means or embedding scattering particles around the outer surface of the core or within the cladding. Such techniques typically result in a decrease in the mechanical integrity of the fiber and frequently are incapable of achieving a wide range of light distributions.

Another conventional technique employs the use of a transmissive medium such as an epoxy with embedded scattering particles and a reflector at the tip. The reflector serves to both improve homogeneity of the light exiting the fiber as well as prevent significant forward light propagation. However, the use of metallic or dielectric reflectors or plugs limits the utility of such sensors because such reflectors may absorb light energy and lead to fiber failure. Moreover; metal reflectors, in particular, may not be compatible with new magnetic resonance imaging (MRI) image-guided procedures. A further disadvantage is that such reflectors may be difficult or expensive to produce. Finally, the reflector and scattering medium, being of significantly different materials with differing mechanical properties, may partially or fully separate at their interface, leading to potential "hot spots," undesirable light distributions, or degradation of diffuser performance, all of which are likely to lead to a failure in the applicator Another conventional technique employs a cylindrical diffusing tip that includes an optically transparent core material such as silicone with scattering particles dispersed therein which abuts the core of the optical fiber. This diffusing tip is manufactured such that the concentration of scattering particles continuously increases from the proximal to distal ends of the diffusing tip. The increase in the concentration of scattering particles eliminates the need for a reflector because light is increasingly scattered along the diffusing tip length while the amount of light available decreases distally. However, this conventional technique has a number of limitations. For one, the gradient in the tip is extruded using a two-channel injector system with a mixing chamber whose contents are combined and extruded through a die. The contents are combined by varying the relative feed rates of elastomer with two different concentrations of scatterers to create a gradient in the scattering particles along the axial length of the diffusing tip,. This mixing process places fundamental limitations on the range of gradients (e.g., the rate of change of said gradients) which can be produced. Moreover, this mixing process allows for the creation of gradients only in the direction of the axis of the fiber. A radial gradient in scattering particle concentration, for example, is unachievable by this conventional process.

Further, the elastomer-based tip is first extruded as described above, cut to length and then affixed to the end of the terminus face of the delivery fiber. A plastic tube then is slid over both the jacket of the optical fiber and the diffuser core. Thus the diffuser core must be separately affixed to the optical fiber core which results in a small bonding surface area. Further, an outer tube larger than the fiber's outer jacket is required, thereby increasing the overall diameter of the device beyond the outer diameter of the fiber's outer jacket. Another disadvantage related to affixing the tip in this manner is that there are no bonding interfaces to any circumferential surfaces of the fiber. The sole axial bond is vulnerable to defects such as air gaps, especially when flexion occurs at the interface between the optical fiber core and diffuser core that causes the two to separate Air or other gaps between the optical fiber core and diffuser core change the intended light distribution and may result in unintended "hot spots" which significantly increase the risk of fiber failure during use. Gaps or defects in the interface between the diffusing core and the plastic tube placed over the core may also lead to "hot spots," degradation of diffuser uniformity, and a decrease in power handling capability.

Accordingly, a light diffusing tip that overcomes the limitations of conventional light diffusing tips would be advantageous.

BRIEF DESCRIPTION OF THE DRAWINGS

The purpose and advantages of the present disclosure will be apparent to those of ordinary skill in the art from the following detailed description in conjunction with the appended drawings in which like reference characters are used to indicate like elements, and in which.

DESCRIPTION OF THE DRAWINGS

FIGS. 1-14 illustrate various exemplary light diffusing applicators and exemplary methods of their use and manufacture. The devices and methods described herein may find advantageous application in the treatment of solid cancerous tumors and other defects in soft tissue. In at least one embodiment of the disclosures made herein, a light diffusing applicator includes an optical waveguide designed for connection to an energy source and further includes an optical diffusing tip designed to cause cylindrical or substantially cylindrical scattering of light radiation around the axis of the optical waveguide.

The term light, as used herein, refers to electromagnetic radiation within any of the infrared, visible, and ultraviolet spectra. Consequently, the term light transmissive, as used herein, is used in the context of the type of light implemented Exemplary sources of light may include, but are not limited to, lasers, light emitting diodes, arc lamps, light bulbs, flash lamps, and the like.

Figure 1:
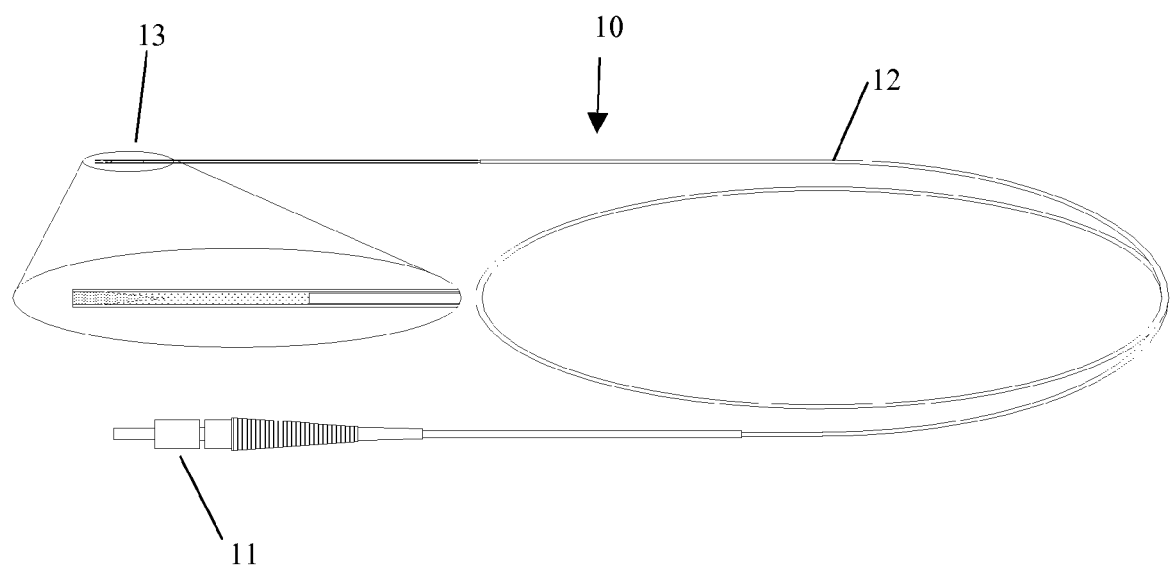
FIG. 1 is a schematic diagram illustrating an exemplary light applicator in accordance with at least one embodiment of the present disclosure.

Referring now to FIG. 1, an exemplary light applicator 10 is illustrated in accordance with at least one embodiment of the present disclosure The light applicator 10 includes a connector 11 coupled to a proximal end of a flexible optical waveguide 12 and a light diffusing tip 13 optically and mechanically coupled to a distal end of the optical waveguide 12. The connector 11 couples to a light source (not shown) to receive light energy for transmission to the diffusing tip 13 via the waveguide 12. An example of the connector 11 includes the SMA905 fiber connector (available from Amphenol-Fiber Optic Products of Lisle, Ill.) which is frequently used for stable and reliable coupling to common lasers and other light sources. The diffusing tip 13, in turn, scatters the light energy over a substantial portion of the diffusing tip 13. As disclosed in greater detail herein, in at least one embodiment, the diffusing tip 13 comprises a light transmissive housing having a monolithic scattering medium disposed within the housing, where the monolithic scattering medium includes two or more distinct scattering regions, each scattering region comprising a scattering material having scattering properties different from the scattering properties of the remaining scattering regions. Additionally, each scattering region may be coextensive along a length of the tubing with one or more adjacent scattering regions so that the diffusing tip exhibits a gradient in its scattering coefficient both axially and radially.

Figure 2:
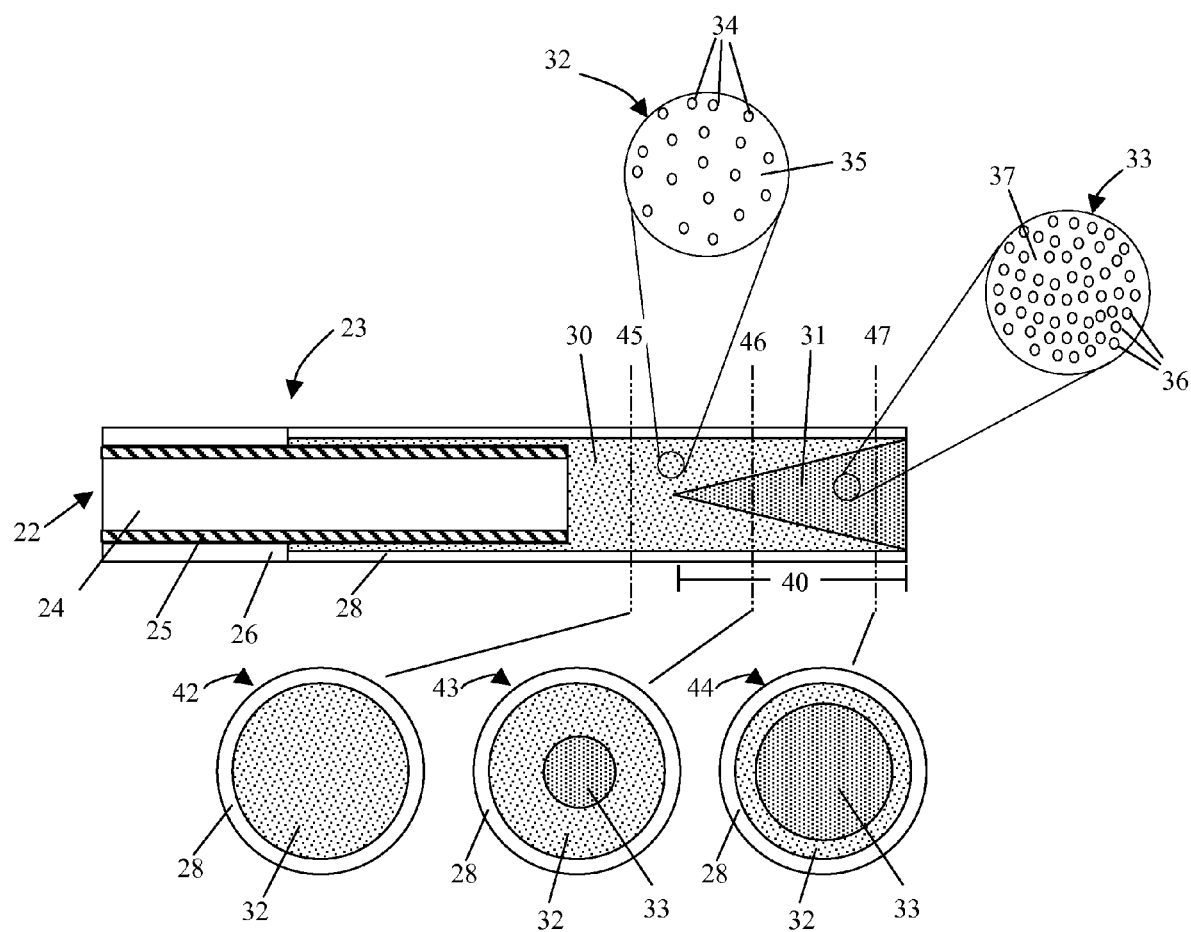
FIGS. 2-7 and 9 are cross-section views illustrating various exemplary light diffusing tips in accordance with various embodiments of the present disclosure.

Referring now to FIG. 2, an exemplary implementation of a light diffusing tip is illustrated in accordance with at least one embodiment of the present disclosure The illustrated diffusing tip 23 includes an optical waveguide 22 having one or, more optical fiber cores 24 surrounded by a cladding layer 25 and protective jacketing 26. A portion of the distal end of the optical waveguide 22 may be stripped of its outer protective jacketing 26, thereby exposing the cladding 25 over a length of the fiber. In the illustrated example, the distal end of the optical waveguide 22 is cleaved or polished flat, but other termination configurations, such as termination in a point, ball or at an angle, may be implemented as appropriate. The diffusing tip 23 further includes an outer housing 28 to enclose scattering material and to provide a surface for bonding the diffusing tip 23 to the optical waveguide 22. The outer housing 28 preferably is composed of any of a variety of light transmissive materials, such as, for example, flexible PTFE or "Teflon," polycarbonate, polyurethane, polyethylene, polypropylene, silicon, nylon, PVC, PET, ABS, PES, PEEK, FEP, as well as other flexible or rigid, radio-opaque or non radio-opaque materials as appropriate.

Disposed within the housing 28 is scattering material forming a monolithic scattering medium having two or more regions, where each region comprises a scattering material having one or more scattering properties that are distinct from the scattering properties of the scattering materials of the other regions In the illustrated example of FIG. 2, the monolithic scattering medium disposed within the housing 28 includes two scattering regions 30 and 31 The scattering region 30 includes a scattering material 32 having one or more scattering properties that are distinct from the scattering material 33 comprising the scattering region 3 1. In at least one embodiment, the scattering material 32 of the scattering region 30 comprises scattering particles 34 suspended in a light transmissive material 35 and the scattering material 33 comprises scattering particles 36 suspended in a light transmissive material 37. Examples of materials suitable for the scattering particles 34 and 36 include, but are not limited to plastics, glasses, metals, metal oxides, or other particles known in the art to scatter optical radiation. An exemplary commercial product which may be implemented as scattering particles 34 or 36 includes titanium dioxide particles available from Sigma-Aldrich Co. of St. Louis, Mo. Examples of materials suitable for the light transmissive materials 35 and 37 include, but are not limited to, plastics (such as described above with reference to the housing 28), epoxies, and elastomers such as silicone or cyanoacrylates. An exemplary commercial product which may be implemented as materials 35 or 37 includes Mastersil 151 two-part silicone epoxy available from Master Bond, Inc., of Hackensack, N.J. As depicted by FIG. 2, the scattering material 32 (or, alternatively, the scattering material 33) further may be used as an adhesive to bond the housing 28 to the fiber core 24 and/or cladding 26.

As noted above, the scattering material 32 and the scattering material 33, in one embodiment, have one or more different scattering properties. Different scattering properties between the scattering materials 32 and 33 may be implemented by, for example, utilizing one type of scattering particle 34 (e.g., titanium dioxide) for scattering material 32 and a different type of scattering particle 36 (e.g., gold particles) for scattering material 33. As another example, the scattering particles 34 and 36 may be of different sizes and/or shapes so as to exhibit different scattering properties. As a further example, the concentration of the scattering particles 34 in the material 32 may be different than the concentration of scattering particles 36 in the material 37 so that the scattering materials 32 and 33 exhibit different scattering properties. It also should be noted that other configurations like gas bubbles in the elastomer or an emulsified liquid also may create scattering centers. Different scattering properties also may be achieved using light transmissive materials with different indexes of refraction. The scattering materials 32 and 33 also may be different from each other by a combination of any of scattering particle type, scattering particle size, scattering particle shape, scattering particle concentration or a transmissive material's index of refraction. Typically, the difference between the scattering properties of the two materials 32 and 33 is represented by a difference in their scattering coefficients (i.e., a measure of the amount of light scattering exhibited by a material).

In at least one embodiment, the scattering materials 32 and 33 are positioned within the housing 28 such that the scattering regions 30 and 31 are coextensive for, at least a portion 40 of the length of the housing 28. In the example illustrated in FIG. 2, the scattering regions 30 and 31 are arranged such that the scattering region 31 forms a substantially cone shaped portion that is at least partially surrounded by material of the scattering region 30, and thus the scattering regions 30 and 31 are coextensive along the housing 28 for part or all of the cone shaped region. As discussed in greater detail herein, the scattering regions 30 and 31 may be formed so as to take on any of a variety of shapes in the coextensive portion 40 of the housing 28 as appropriate.

As illustrated by cross-sections 42-44 at positions 45-47, respectively, of diffusing tip 23, the geometric relationship between the two scattering regions 30 and 31 varies. As the distance from the termination of the fiber core 24 increases, the cross-sectional area of the scattering material 32 decreases while the cross-sectional area of the scattering material 33 increases At point 45, the scattering medium of the diffusing tip is made up of the scattering material 32,. At point 46, the amount of scattering material 32 present decreases and the amount of scattering material 33 increases. At point 47, the scattering element of the diffusing tip 23 is almost entirely made up of the scattering material 33. Thus, the proportion of the scattering material 33 to the scattering material 32 (i.e, the proportion of the scattering region 31 to the scattering region 30) of the monolithic scattering medium generally increases from the proximal end to the distal end of the diffusing tip 23. The distal end of diffusing tip 23 may be made up entirely of scattering material 33.

The concentration and length of both the scattering region 30 and the scattering region 31 within the diffusing tip 23 may be varied to achieve a desirable light distribution. For example, longer diffusing tips may have lower concentration scattering regions or shorter lengths of higher concentration scattering regions. Similarly, shorter diffusing tips may contain a shorter length of a low concentration scattering region and a longer length of a higher concentration scattering region.

The concentration and length of each scattering region preferably is selected to result in substantially uniform emission of light along the length of the diffusing tip. The intensity of light in a partially transmissive (i.e., scattering and/or absorptive) medium typically exhibits a fall-off described by Beer's Law, $I=I_o e^{-\mu z}$, where I represents intensity at z, Io represents initial intensity, $\mu$ represents attenuation coefficient and z represents distance away from the source. Accordingly, the characteristics of the scattering regions may be chosen so as to make the light scattered along the length of the diffusing tip approximately constant in view of Beer's Law. To illustrate, scattering regions may be arranged so that the effective scattering coefficient $\mu(z)=-\log(1-z/L)/z$, for $z\epsilon[0, L]$. This may be achieved by, for example, arranging the scattering regions such that the overlapping segments have profiles substantially related by the preceding equation. As another example, the scattering material 32 may have a lower concentration of scattering particles 34 than the concentration of scattering particles 36 of the scattering material 33 and, therefore, the effective concentration of scattering particles increases over the coextensive portion 40 even as the intensity of the light energy decreases. However, in certain instances it may be desirable to preferentially emit light over a given cross section of the diffusing tip 23 which may be accomplished by concentrating scattering material having higher scattering coefficients at positions where more light is intended to exit the diffusing tip 23.

Figure 3:
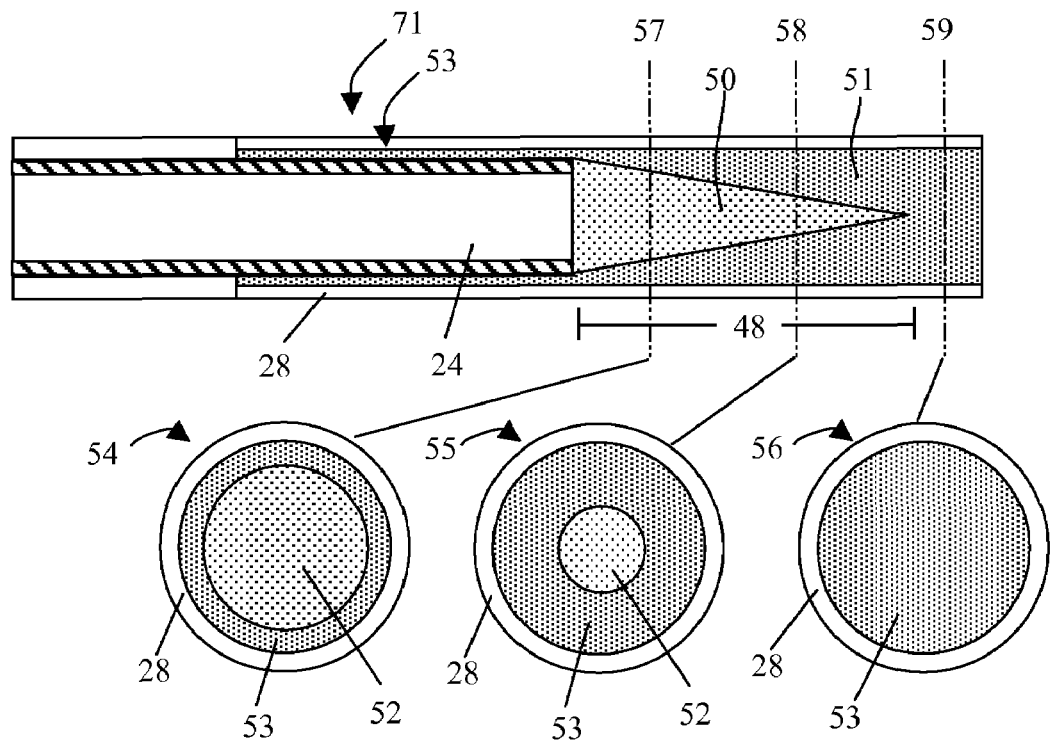
Figure 4:
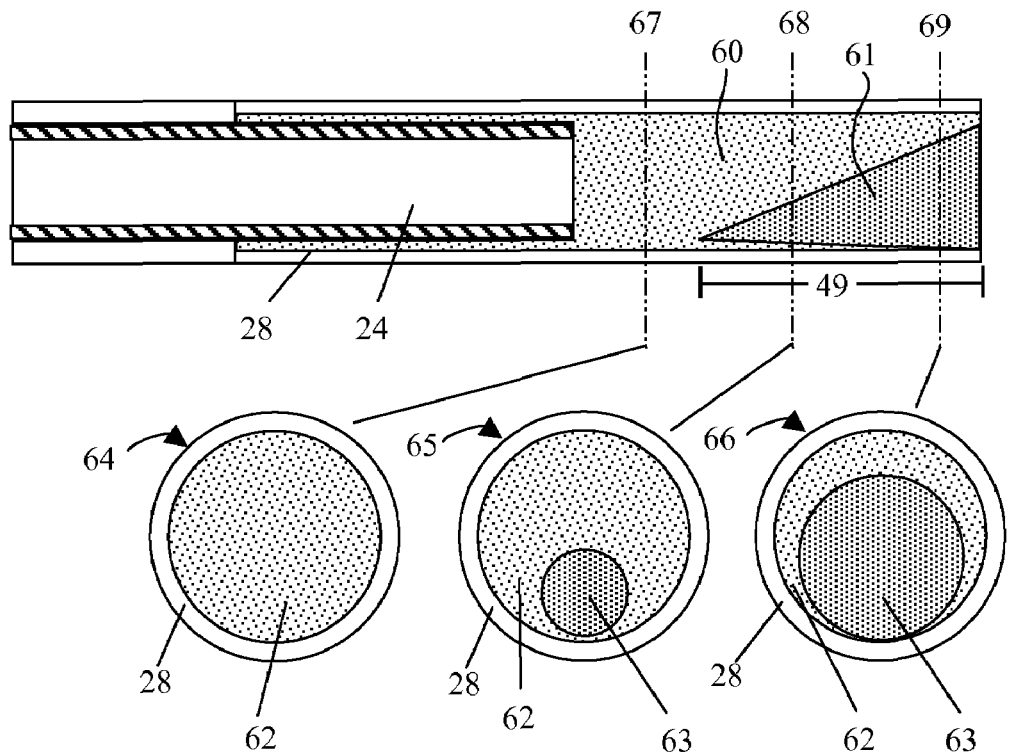

Referring now to FIGS. 3 and 4, alternate exemplary implementations of a light diffusing tip are illustrated in accordance with at least one embodiment of the present disclosure. FIG. 3 illustrates a diffusing tip 71 comprising a monolithic scattering medium disposed within the housing 28 and having two scattering regions 50 and 51. In contrast with the diffusing tip 23 of FIG. 2, the scattering region 50 includes a scattering material 52 having a substantially conical portion directed away from the termination of the fiber core 24 and the scattering region 51 includes a scattering material 53 having a region that at least partially surrounds the conical region and is therefore coextensive with the scattering material 52 over the portion 48 of the length of the diffusing tip 71 In the illustrated embodiment, the scattering material 52 has a lower scattering coefficient than the scattering material 53. As the cross-sections 54-56 at positions 57-59, respectively, illustrate, the proportion of the scattering material 52 to the scattering material 53 decreases, and the effective scattering coefficient therefore increases, as the distance from the termination of the fiber core 24 increases.

FIG. 4 illustrates another exemplary implementation of a diffusing tip having a monolithic scattering medium with two or more partially overlapping, distinct scattering regions. FIG. 4 illustrates an exemplary diffusing tip having distinct scattering regions 60 and 61, wherein the scattering region 61 comprises a substantially conical region surrounded by the scattering region 60 over portion 49. The scattering region 60 comprises a scattering material 62 having a first scattering property and the scattering region 61 comprises scattering material 63 having a second scattering property different from the first scattering property. Whereas the exemplary diffusing tips 23 and 71 of FIGS. 2 and 3 are illustrated as having scattering regions that include conical portions substantially coaxial with the axis of the housing 10, the axis of the substantially conical portion of scattering region 60 is offset from the longitudinal axis of the housing 28, as illustrated by cross-sections 64-66 at positions 67-69, respectively. Such an implementation may be employed to preferentially scatter light out of a given angular region of the diffusing tip. During the manufacture the diffusing tip, the scattering region 61 can be formed by allowing the scattering materials 62 and 63 to cure in the horizontal position or in a centrifuge, where the conical region 61 may settle due to gravity or centrifugal force.

Figure 5:
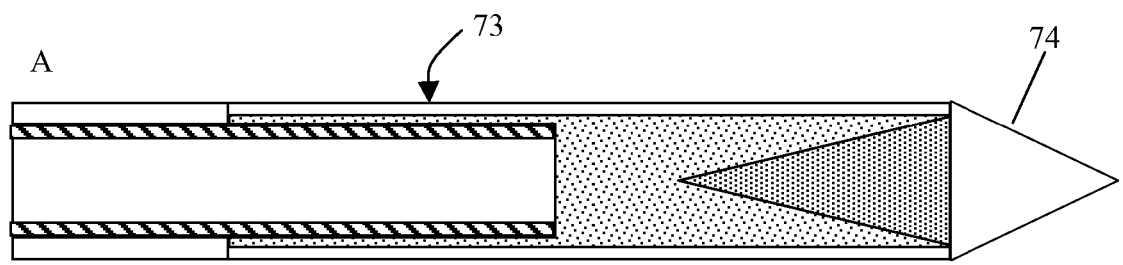
Figure 6:
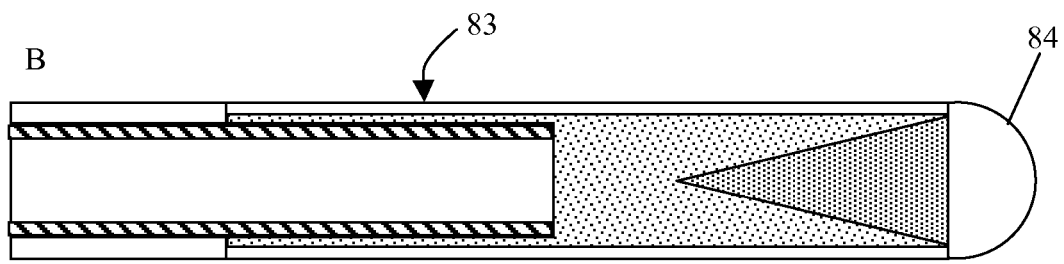
Figure 7:
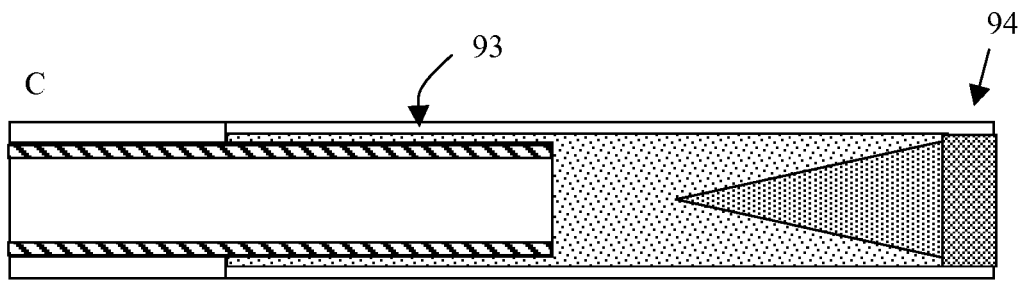

Referring now to FIGS. 5-7, exemplary diffusing tips having various caps secured to their distal ends are illustrated in accordance with at least one embodiment of the present disclosure. FIG. 5 depicts a diffusing tip 73 having a pointed cap 74 that facilitates insertion of the fiber into tissues for interstitial applications. FIG. 6 depicts a diffusing tip 83 having a rounded cap 84 that may be used in hollow organs or to minimize risk of vessel punctures during interstitial applications FIG. 7 depicts a diffusing tip 93 having a blunt cap 94 that represents a third scattering region having a scattering material with a high scattering coefficient for further minimizing forward propagation of light from the distal end of the diffusing tip 93. Blunt cap 94 may also be made of a biocompatible material to prevent contact of scattering material with bodily tissue.

Figure 8:
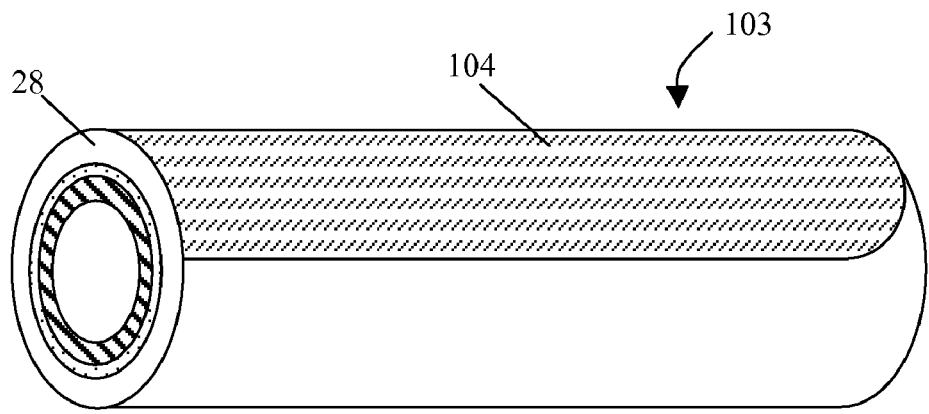
FIG. 8 is an isometric view illustrating an exemplary light diffusing tip having reflective material overlaying a portion of the tip in accordance with at least one embodiment of the present disclosure.
Figure 9:
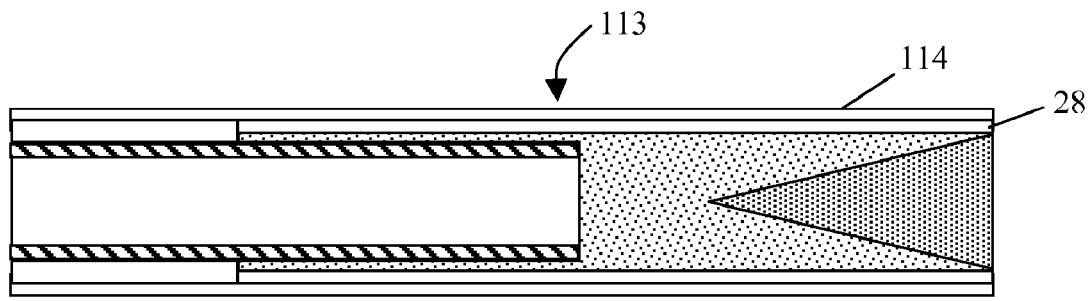
Figure 10:
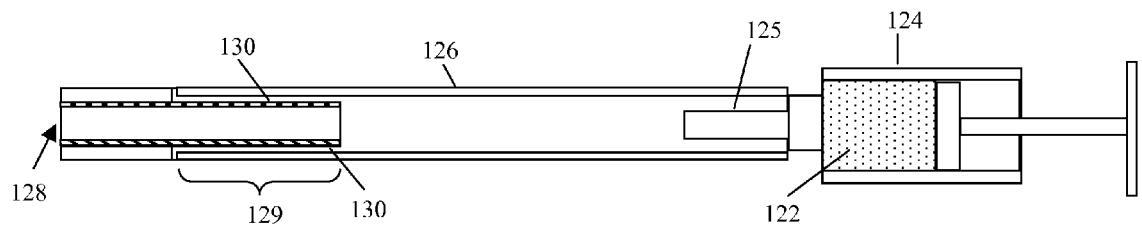
FIGS. 10-13 are cross-section views illustrating an exemplary method of manufacturing a light diffusing tip in accordance with at least one embodiment of the present disclosure.

Referring now to FIGS. 8 and 9, exemplary treatments to the housing of the diffusing tip are illustrated in accordance to at least one embodiment of the present disclosure. FIG. 8 depicts an exemplary diffusing tip 103 with a selective angular emission profile that is achieved using a reflective material 104 overlaying a section of the surface of the housing 28 of the diffusing tip 103, where the reflective material 104 prevents light energy from passing through that section. Suitable materials for the reflective material 104 include, for example, deposited surfaces of gold, silver, aluminum, chrome, nickel, or other reflective materials. The reflective material 104 may be disposed either on the inner surface or outer surface of the housing 28. FIG. 9 depicts an exemplary diffusing tip 113 having a non-stick coating 114 disposed on some or all of the outer surface of the housing 28. The non-stick coating 114 may include, for example, any of a number of light transmissive fluoropolymers with high temperature handling capability and non-stick surface properties with respect to thermally coagulated tissues Materials for the housing 28 can then be chosen based on the desired stiffness of the diffusing tip while the non-stick coating 114 of fluoropolymer provides the ideal surface properties. Alternatively, the non-stick coating 114 may be used to provide increased stiffness or durability for the diffusing tip 113.

Referring now to FIGS. 10-13, an exemplary method for manufacturing a light diffusing tip is illustrated in accordance with at least one embodiment of the present disclosure Initially, a scattering material having a lower scattering coefficient is created, for example, by mixing a lower amount of scattering particles in an elastomer material to create a scattering material with a lower concentration of scattering particles. A scattering material having a higher scattering coefficient also is created. The scattering material having a higher scattering coefficient may be created by, for example, mixing a higher amount of scattering particles in an elastomer material to create a scattering material having a higher concentration of scattering particles. To illustrate, the scattering particle and elastomer mixtures may include, for example, titanium dioxide particles mixed in silicone epoxy. In order to minimize or eliminate air bubbles in the scattering materials, a vacuum may be applied to the uncured silicone/titanium dioxide mixture prior to use.

In certain instances, the scattering particle concentration range for the lower scattering coefficient material and the higher scattering coefficient material varies depending on the length and core diameter of the optical waveguide. For a typical 400 micron core diameter optical waveguide, a diffusing tip of for example, 10 mm in length typically has a lower scattering coefficient material with a concentration of $TiO_2$ scattering particles preferably between 100 mg/ml and 180 mg/ml and more preferably between 145 mg/ml and 155 mg/ml. The higher scattering coefficient material typically has a concentration of $TiO_2$ scattering particles preferably between 2500 mg/ml and 6500 mg/ml and more preferably between 4400 mg/ml and 4650 mg/ml. The scattering regions formed from the scattering materials also may vary in length To illustrate, for the same 10 mm long diffusing tip, the length of the scattering region resulting from the lower scattering coefficient material preferably is between 1 mm and 100 mm, more preferably between 5 mm and 10 mm and even more preferably is about 6 mm. For the same diffusing tip length, the length of the scattering region formed from the higher scattering coefficient material preferably is between 1 mm and 100 mm, more preferably is between 2 mm and 5 mm and even more preferably is about 4 mm. The shapes and lengths of each scattering region and the concentration of each scattering material may be varied to achieve the desired output profile for light emitted from the diffusing tip, Referring to FIG. 10, lower scattering coefficient material 122 is transferred to a first injector barrel 124 (e.g., a 3 cc barrel available from EFD, Inc. of East Providence, R.I.) supplied with a blunt ended needle 125 (e.g., a 27 Ga needle available from EFD, Inc.). A housing 126 is positioned over the distal end of an optical waveguide 128 over a length where the protective jacket has previously been removed from the optical waveguide 128. In at least one embodiment, the housing 126 includes a tubular housing having an outer diameter selected to substantially match the outer diameter of the optical waveguide's protective jacket so that a uniform surface profile is provided along the entire length of the resulting light applicator The wall thickness of the housing 126 may be selected to allow space for a bonding region 130 between the inner wall of the housing 126 and the exposed cladding on the optical waveguide 128.

Figure 11:
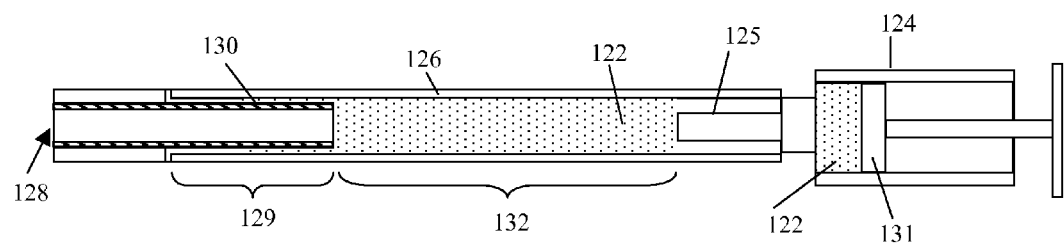

Referring to FIG. 11, the needle 125 is introduced into the distal end of the housing 126 and a plunger tip 131 within barrel 124 is actuated either manually or using a regulated dispenser (for example, the EFD Ultra Dispenser available from EFD, Inc.) to inject lower scattering coefficient material 122 into the lumen of the housing 126. The lower scattering coefficient material 122 may be injected until, for example, the distance 132 between the end of the optical waveguide 128 and the blunt ended needle 125 and approximately half the length 129 of housing 126 covering the exposed end of the optical waveguide 128 are filled. At this point, the needle 125 may be removed from the distal end of the housing 126 while continuing to inject.

Figure 12:
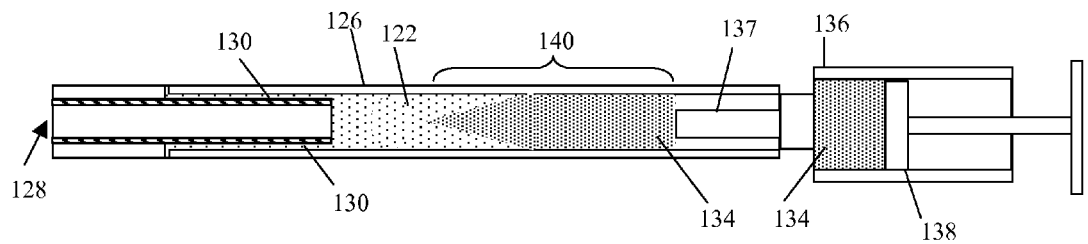

Referring to FIG. 12, the higher scattering coefficient material 134 is transferred to a second injector barrel 136 supplied with a second blunt ended needle 137. The needle 137 then is positioned inside the distal end of the housing 126. Actuation of plunger tip 138 infuses higher scattering coefficient material 134 into a portion of the lower scattering coefficient material 122 which results in the formation of a discrete substantially cone-shaped portions of higher scattering coefficient material 134 within the lower scattering coefficient material 122 over a length 140 of the housing 126. During injection of higher scattering coefficient material 134, lower scattering coefficient material 122 is forced toward the optical waveguide 128 and allowed to fill the bonding region 130 between the housing 126 and the exposed cladding of the optical waveguide 128. At this point the needle 137 is removed from the housing 126 while continuing to inject. Alternatively, the higher scattering coefficient material 134 may be inserted via the proximal end of the housing 126 and the optical waveguide 128 subsequently inserted before or during the curing of the scattering material 134.

Figure 13:
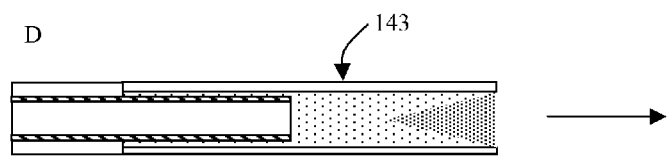
Figure 13:
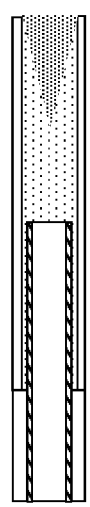
Figure 14:
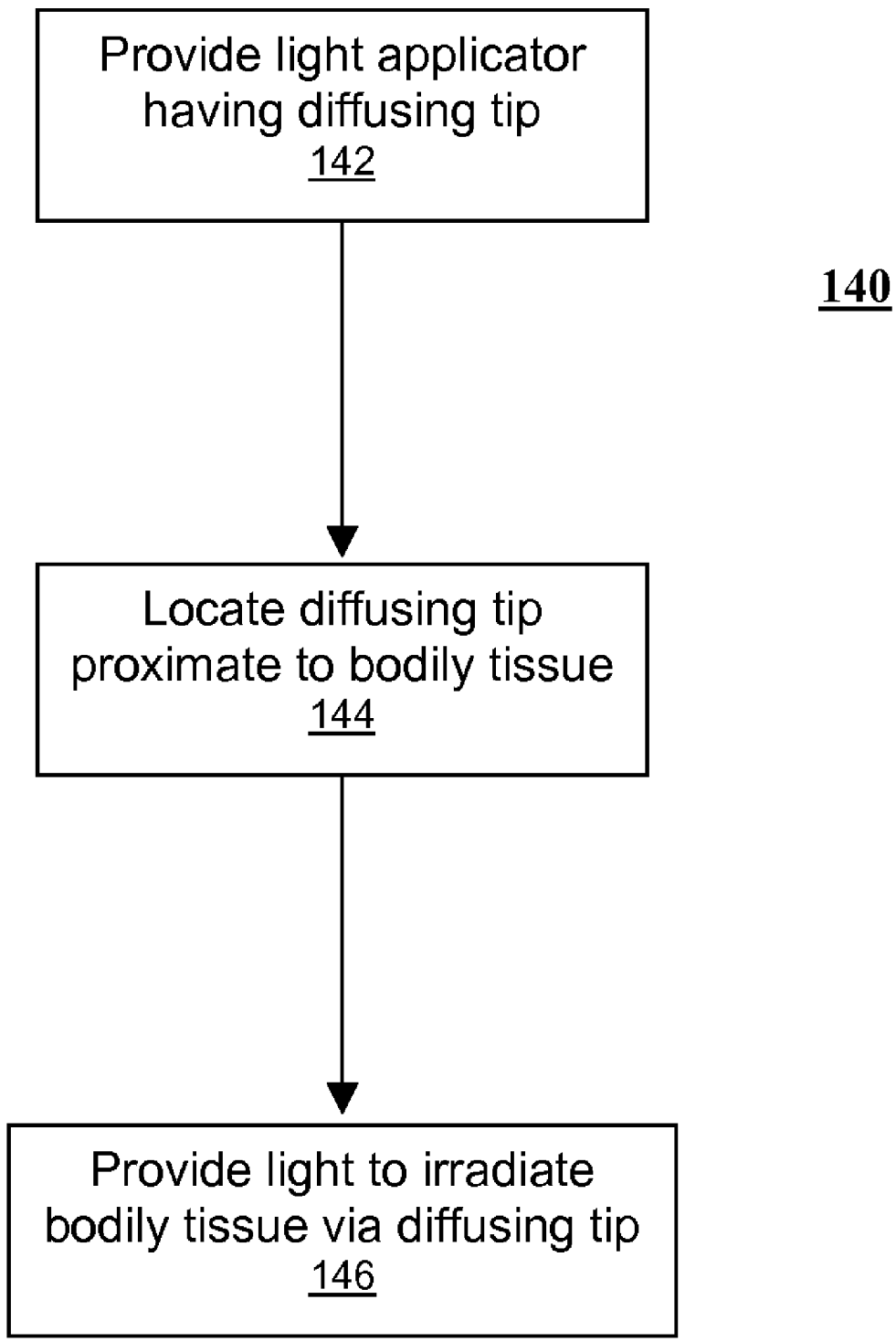
FIG. 14 is a flow chart illustrating an exemplary method for utilizing a light applicator in accordance with at least one embodiment of the present disclosure.

As illustrated by FIG. 13, the distal end of the resulting diffusing tip 143 may be cut or otherwise trimmed to the appropriate length, and the finished tip/fiber assembly may be positioned vertically and the scattering materials 132 and 134 allowed to cure. Alternatively, the diffusing tip 143 may be placed in a horizontal position or subjected to a centrifuge so as to cause the scattering particles of the scattering materials 132 and 134 to settle in one or more desired locations Thus, as FIGS. 10-13 illustrate, although injected as two separate preparations, the scattering materials 132 and 134 may be formulated of the same base material and thus cure into a monolithic scattering medium with spatially varying (both longitudinally and radially) scattering particle concentrations.

Although FIGS. 11-13 illustrate an exemplary method for manufacturing a diffusing tip, other techniques may be implemented without departing from the spirit or the scope of the present invention. For example, the diffusing tip may be formed by inserting one type of scattering material into the housing 126 and allowing the scattering material to partially or fully cure. A cavity is then formed in one end of the scattering material using, for example, a drill bit or scraping tool. Alternatively, a mold having the desired cavity shape may be inserted into one end of the scattering material prior to curing and then removed after the first scattering material has at least partially cured. Another type of scattering material then is inserted into the housing 126 so that it occupies the cavity in formed the first scattering material. The second scattering material then may be left to cure and bond to the first scattering material so as to form the scattering medium of the resulting diffusing tip.

While several specific geometric shapes and relationships for the discrete scattering regions have been disclosed herein, any suitable arrangement of scattering regions may be implemented using the teachings provided herein without departing from the spirit or scope of the present disclosure. For example, the shape of the a scattering region is generally described herein as being conical in shape and increasing linearly in size from proximal to distal ends, but alternatively its shape could have a non-linear taper, such as in accordance with Beer's Law, or other geometric shape and still achieve a desired effect. As such, there are many suitable modifications and variations in the shapes, sizes, lengths, and positional arrangements of the discrete scattering regions that are within the scope of the present disclosure Referring now to FIG. 14, an exemplary method 140 of use of a light applicator having a diffusing tip is illustrated in accordance with at least one embodiment. Generally, the exemplary method 140 initiates at step 142 wherein a light applicator having a diffusing tip (e.g., the light applicator 10 of FIG. 1) is obtained. The light applicator then may be affixed or otherwise coupled to a light source via the connector 11 (FIG. 1). At step 144, the diffusing tip is placed on or in a patient and the light diffusing tip is located proximate to the bodily tissue to be treated. At step 146, the light source is activated and light energy is transmitted to the diffusing tip 13 (FIG. 1) via the connector 11 and the optical waveguide 12 (FIG. 1). Upon reaching the diffusing tip 13, the light is scattered along and out of the monolithic scattering medium in accordance with the scattering properties of the two or more distinct scattering regions of the monolithic scattering medium so as to irradiate the bodily tissue proximal to the diffusing tip 13. As noted above, in one embodiment, the two or more scattering regions have particular scattering properties and overlap in such a way so as to provide a substantially uniform light scattering along the length of the diffusing tip. In other embodiments, the scattering regions may be arranged so as to concentrate the light scattering in certain areas or in certain directions. Specific implementations of the general method 140 may include, for example LITT treatment of focal or metastatic tumors in brain, prostate, kidney, liver, breast, uterine, spinal, bone or other organs, as well as photodynamic therapy in hollow organs.

The previous description is intended to convey a thorough understanding of the present disclosure by providing a number of specific embodiments and details involving light diffusion techniques. It is understood, however, that the present disclosure is not limited to these specific embodiments and details, which are exemplary only. It is further understood that one possessing ordinary skill in the art, in light of known systems and methods, would appreciate the use of the disclosure for its intended purposes and benefits in any number of alternative embodiments, depending upon specific design and other needs.

What is claimed is:

1. A method comprising:
   providing a housing;
   forming a monolithic light scattering medium within the housing, the monolithic light scattering medium including a first scattering region having a first scattering property and a second scattering region having a second scattering property different from the first scattering property, wherein the first scattering region and the second scattering region are coextensive along a substantial portion of a length of the housing.

2. The method of claim 1, wherein forming the monolithic light scattering medium comprises:
   inserting a first scattering material into a first end of the housing to form the first scattering region, the first scattering material having the first scattering property; and
   inserting a second scattering material into the housing so as to contact a portion of the first scattering region over a substantial portion of the length of the housing to form the second scattering region, the second scattering material having the second scattering property; and
   curing the first scattering material and the second scattering material to form a monolithic scattering medium.

3. The method of claim 2, wherein inserting the second scattering material includes inserting the second scattering material to displace at least a portion of the first scattering material.

4. The method of claim 3, wherein inserting the second scattering material includes inserting the second material to form a conical shape.

5. The method of claim 2, wherein the first scattering material includes a first concentration of scattering particles suspended in a light transmissive material and the second scattering material includes a second concentration of the scattering particles suspended in a light transmissive material.

6. The method of claim 2, wherein the first scattering material includes a first type of scattering particle suspended in a light transmissive material and the second scattering material includes a second type of scattering particle suspended in a light transmissive material.

7. The method of claim 2, further comprising:
   inserting a portion of at least one optical waveguide into one of the first or second scattering materials prior to curing.

8. A method of forming an applicator, the method comprising:

inserting a first scattering material into a first end of a housing to form a first scattering region, the first scattering material having a first scattering property; and inserting a second scattering material into the housing so as to contact a portion of the first scattering region over a substantial portion of the length of the housing to form a second scattering region, the second scattering material having the second scattering property; and curing the first scattering material and the second scattering material to form a monolithic scattering medium.

9. The method of claim 8, further comprising mixing a scattering material at a concentration of 100 mg/ml to 180 mg/ml with a polymer to form the first scattering material.

10. The method of claim 8, further comprising mixing a scattering material at a concentration of 2500 mg/ml to 6500 mg/ml with a polymer to form the second scattering material.

11. The method of claim 8, further comprising applying a vacuum to the first scattering material and to the second scattering material prior to curing the first scattering material and the second scattering material.

12. The method of claim 8, wherein inserting the second scattering material includes inserting the second scattering material to displace at least a portion of the first scattering material.

13. The method of claim 12, wherein inserting the second scattering material includes inserting the second material to form a conical shape.

14. The method of claim 13, wherein the conical shape is coaxial with the housing.

15. The method of claim 13, wherein the conical shape is offset from the longitudinal axis of the housing.

16. The method of claim 8, wherein the second scattering material is inserted into the first end of the housing.

17. The method of claim 8, further comprising positioning the housing horizontally while curing the first and second scattering materials.

18. The method of claim 8, wherein the housing is subjected to a centrifuge while curing the first and second scattering materials.

19. The method of claim 8, further comprising:

inserting a portion of at least one optical waveguide into one of the first or second scattering materials prior to curing.

20. A method comprising:

providing a light applicator having a light diffusing tip coupled to a first end of an optical waveguide of the light applicator, the light diffusing tip comprising a housing and a monolithic light scattering medium disposed within the housing, the light scattering medium including a first scattering region having a first scattering property and a second scattering region having a second scattering property different from the first scattering property, wherein the first scattering region and the second scattering region are coextensive along a substantial portion of a length of the housing;

locating the light diffusing tip proximal to a bodily tissue; and providing light energy to the light diffusing tip via a second end of optical waveguide of the light applicator so as to irradiate the bodily tissue.

21. The method of claim 20, wherein the bodily tissue is a tumor.

22. The method of claim 20, wherein the bodily tissue is irradiated as part of photodynamic therapy.

* * * * *